Figure 1:
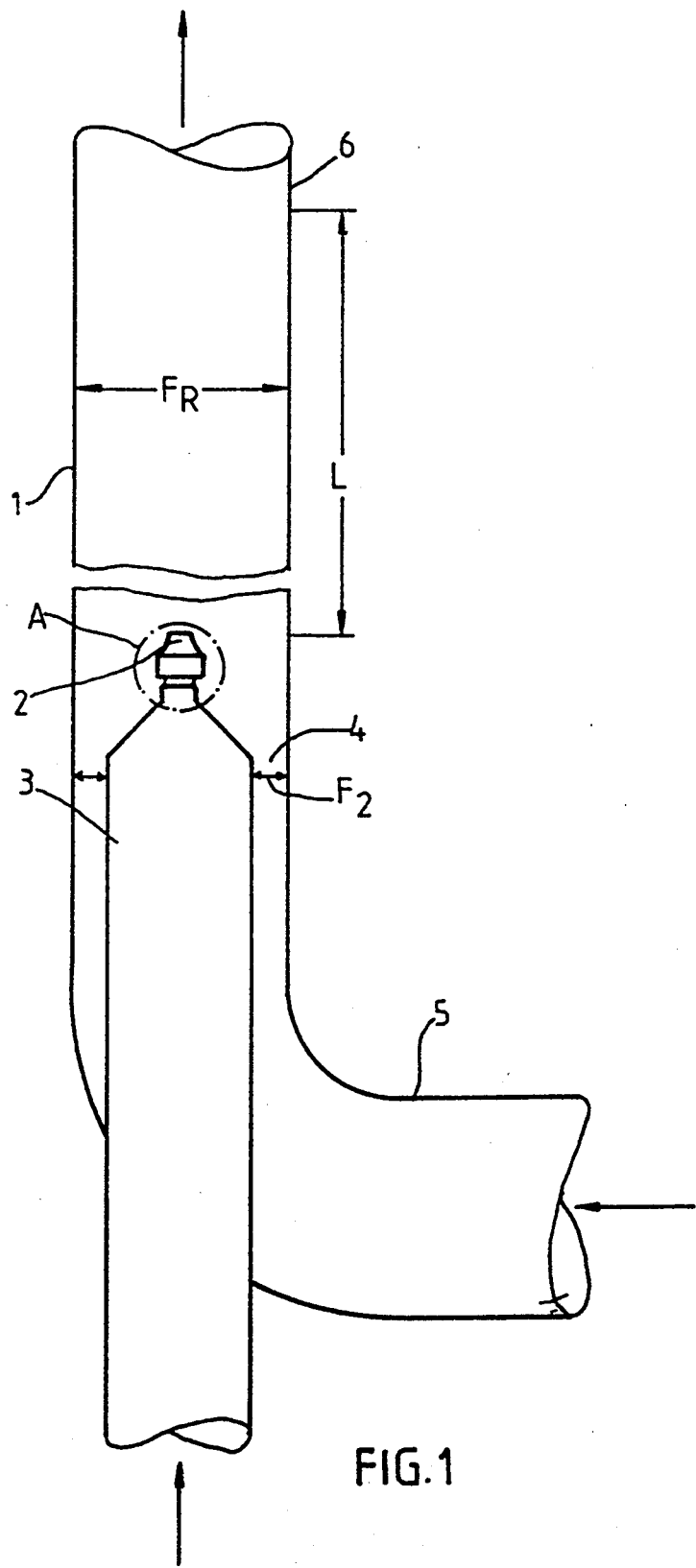

United States Patent [19]

Arnold et al.

[11] Patent Number: 5,420,255
[45] Date of Patent: May 30, 1995

[54] PROCESS FOR THE CONTINUOUS REACTION OF HALOGENOPYRIMIDINES WITH AMINES

[75] Inventors: Siegbert Arnold, Bonn; Hans-Georg Frosch, Koeln; Manfred Hoppe, Kuerten; Wolfgang Müllers, Gladbach; Richard Sommer, Odenthal-Gloebusch, all of Germany

[73] Assignee: Bayer Aktiengesellschaft, Leverkusen, Germany

[21] Appl. No.: 200,865

[22] Filed: Feb. 22, 1994

Related U.S. Application Data

[63] Continuation of Ser. No. 970,897, Nov. 3, 1992, abandoned.

[30] Foreign Application Priority Data

Nov. 13, 1991 [DE] Germany ............... 41 37 291.3

[51] Int. Cl.$^6$ ............ C09B 43/12; C09B 62/20; C07D 239/42
[52] U.S. Cl. ............... 534/598; 534/618; 534/625; 534/632; 534/635; 534/636; 534/637; 534/638; 540/125; 544/76; 544/294; 544/327
[58] Field of Search ........... 534/598, 618, 625, 632, 534/635–638; 540/125; 544/76, 294, 327

[56] References Cited

U.S. PATENT DOCUMENTS 4,189,576  2/1980  Altorfer et al. ............... 544/211
4,740,597  4/1988  Franke et al. ............... 534/618 X
4,785,081  11/1988  Franke ........................ 534/598
5,091,515  2/1992  Herd et al. ................... 534/598

FOREIGN PATENT DOCUMENTS 0043927  1/1982  European Pat. Off. .

OTHER PUBLICATIONS

*Journal of Fluorine Chemistry*, vol. 20, 1982, pp. 507–514; R. D. Chambers et al., "Mechanisms for Reactions of Halogenated Compounds ... ".

*Dyes and Pigments*, vol. 3, 1982, pp. 183–190; R. D. Chambers, "Fluorinated Heterocyclic Compounds".

Derwent Abstract of Japanese Pat. No. 57-31,960 Feb. 20, 1982.

*Primary Examiner*—Mary C. Lee
*Assistant Examiner*—Fiona T. Powers
*Attorney, Agent, or Firm*—William C. Gerstenzang; Sprung Horn Kramer & Woods

[57] ABSTRACT

A process for the continuous reaction of halogenopyrimidines with amines, a halogenopyrimidine and an aqueous amine solution or suspension being passed into a reactor and the reaction product being subsequently conducted away, is described, characterized in that the starting materials are introduced into the reactor simultaneously and continuously with intensive mixing.

7 Claims, 1 Drawing Sheet

PROCESS FOR THE CONTINUOUS REACTION OF HALOGENOPYRIMIDINES WITH AMINES

This application is a continuation of application Ser. No. 07/970,897, filed Nov. 3, 1992, now abandoned.

The application relates to a process for the continuous reaction of halogenopyrimidines with amines.

The reactions of halogenopyrimidines with amines are conventionally carried out in a stirred vessel in such a manner that the amine solution or suspension is introduced and the halogenopyrimidine is added under defined conditions. A disadvantage of this procedure is, inter alia, that the halogenopyrimidines are not soluble in the aqueous medium, so that in the resulting two-phase system, in addition to the desired reaction of the halogenopyrimidine with the amino group, hydrolysis of the most reactive halogen atom or atoms occurs, sometimes to a considerable extent. This has the consequence that considerable halogenopyrimidine excesses are sometimes required for complete reaction of the amine.

A further disadvantage of the presently conventional reaction in stirred vessels is that, especially in cases when particularly reactive amines and/or particularly reactive halogenopyrimidines are reacted together, the reaction does not halt at the desired single conversion, but two amine molecules sometimes react to a considerable extent with the halogenopyrimidine.

The aim is to find an improved process for the reaction of halogenopyrimidines with amines, in particular aminonaphtholsulphonic acids.

The present invention relates to a process for the continuous reaction of halogenopyrimidines with amines, halogenopyrimidine and an aqueous amine solution being passed into a reactor and the reaction product being subsequently conducted away, characterised in that the starting materials are introduced into the reactor simultaneously and continuously with intensive mixing.

When the process according to the invention is carried out, the halogenopyrimidines are reacted in finely dispersed form with the amine, by which means the reaction rates are considerably increased. In this case the reaction conditions, principally temperature and pH, can be selected so that the reaction rate can be still further increased without the occurrence to a greater extent of the hydrolysis of the halogenopyrimidine or of the reaction product.

A further advantage is that, with reactive amines and/or halogenopyrimidines, multiple reactions can be avoided, or at least strongly repressed by means of the stoichiometry to be adjusted exactly in the reaction zone.

The halogenopyrimidines can be used in a greater excess, but it is expedient to use halogenopyrimidine/amine molar ratios of 0.8: 1.0 to 1.5: 1, preferably 1: 1 to 1.2: 1, in particular 1: 1 to 1.02: 1.

Suitable reactors are those in which the reactants can be intensively mixed with each other in the stoichiometrically chosen ratio with high energy input with avoidance, or at least minimisation, of back mixing, the reaction conditions, for example temperature and pH, being chosen so that a substantial conversion proceeds even in the reactor.

Suitable reactors are, for example, jet reactors as described in Zehner, P. and Bittins, K.: Fortschr. Verf. Technik D 23, 1985, p. 373–393, in which the starting materials are introduced simultaneously and continuously at different rates into the reactor and, by means of the difference in flow rates, an intensive mixing is effected, and during this, with flow substantially free from back mixing, the reaction is to a considerable extent completed in this reactor.

According to a particular embodiment of the new process, the halogenopyrimidine flows with a Reynolds number of at least 10,000, preferably at least 15,000, and the aqueous amine solution with a Reynolds number of at least 2,500, preferably at least 5,000, into the reactor, the difference in flow rates between the halogenopyrimidine stream and amine solution stream being at least 20 m/s, preferably at least 40 m/s.

These measures ensure a particularly intensive mixing in the quickest way without back flow.

Preferably, a ratio of reactor cross-sectional area to inlet cross-sectional area of the halogenopyrimidine stream of 225 to 40,000, preferably 700 to 12,000, is kept.

By means of this matching of the cross-sectional area ratio to the mass flow ratio, the back flow-free mixing of the reactants is optimised.

The preferred reactor is diagrammatically represented in the drawing diagram 1 and explained in more detail below.

Shown in the drawing are:

FIG. 1 the reactor in section and

Figure 2:
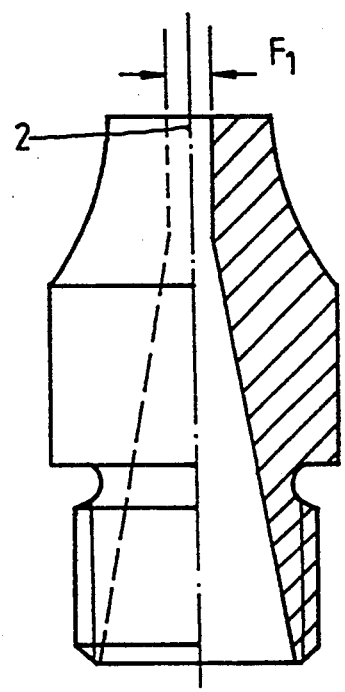

FIG. 2 the nozzle according to detail A in half section in enlarged representation.

A feed line for the halogenopyrimidine opens axially via a nozzle 2 of $F_1 = 0.03$ mm$^2$ cross-sectional area into a reaction tube 1 of $F_R = 80$ mm$^2$ circular cross-sectional area. The feed line is concentrically enclosed by an annular nozzle 4 of $F_2 = 64$ mm$^2$ cross-sectional area, which annular nozzle is connected to a feed line 5 for an aqueous amine solution. The length of the reaction zone L is approximately 250 mm; the connecting tube section 6 serves as transport line for the reaction product.

Instead of an annular nozzle 4, a plurality of individual nozzles or nozzle orifices can also be distributed around the perimeter.

Further suitable reactors are dispersion units of the rotor/stator mixer type.

The residence time in the reactors is sufficient to ensure a considerable degree of conversion even in the reactor.

To complete the reaction, further continuous flow reactors such as for example rotor/stator systems, flow tube possibly fitted with static mixer and stirred vessels can be used. Alternatively, the reaction can also be carried out to completion in discontinuous stirred vessels.

According to a further particular embodiment of the novel process, the reaction is carried out at temperatures of 0° to 90° C., preferably 0° to 50° C.

The amount of alkali in the amine solution is selected so that towards the end of the reaction, a pH between 1 and 11, preferably between 3 and 9, is established.

Preferably, with solutions of amines, in which the amino group is directly bound to the aromatic nucleus, a buffer substance is added, which causes, depending on the buffer substance, a pH between 1 and 8, preferably between 2 and 5 to be maintained during the reaction. Suitable buffer substances are for example alkali metal fluorides or alkali metal phosphates, in particular NaF, Na$_2$HPO$_4$, Na$_3$PO$_4$ or mixtures thereof. These buffer substances are generally used in an amount of 0.2 to 2, preferably 0.4 to 1.2 mol per mole of amine.

If an amine having a chromophore is reacted with a halogenopyrimidine, the reactive dye obtained can be isolated or directly dried without intermediate isolation.

On reaction of a halogenopyrimidine with an amine without a chromophore, the reaction product can be isolated, but it is preferably further processed without intermediate isolation, for example to give reactive dyes, either by subsequent diazotisation and coupling with a coupling component or by reaction with a diazonium salt of an aromatic amine.

This further processing can be carried out discontinuously or continuously in a known manner. By means of the process according to the invention, the condensation products are obtained from the halogenopyrimidines and amines in many cases in significantly higher purity and in higher yields than by using the hitherto conventional processes. This has a positive influence on the quality of the reactive dyes prepared from the condensation products.

Halogenopyrimidines Hal-Z are preferably reacted continuously in special reactors with amines, preferably those containing sulphonyl groups of the formula

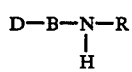
(I)

to give reactive substances or reactive dye precursors of the formula

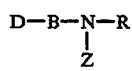
(II)

in which
  B represents a direct linkage or bridge member to an aromatic carbocyclic; C atom of the radical D,
  R represents H, unsubstituted or substituted $C_1$–$C_4$-alkyl (substituents preferably OH, $SO_3H$, $OSO_3H$, Cl, COOH), unsubstituted or substituted phenyl (substituents preferably —$SO_3H$, —COOH, $C_1$–$C_4$-alkyl, halogen), but preferably H,
  D represents a radical of the benzene, naphthalene or heterocyclic series, in particular sulpho group-containing radicals of aromatic amines, which are used as diazo components or coupling components, or the radical of a chromophore, in particular the radical of a dye of the monoazo or polyazo, metal complex azo, anthraquinone, phthalocyanine, formazan, azomethine, dioxazine, phenazine, xanthene, thioxanthone, naphthoquinone, stilbene or triphenylmethane series,
  Z represents mono-, di- and trihalogenopyrimidinyl radicals,
  Hal represents —F, —Cl and —Br.

The reaction is preferably carried out in an aqueous medium with use of an aqueous amine solution or amine suspension.

The sulpho group-containing amines are introduced into the reactor as aqueous solutions or suspensions, the halogenopyrimidines as solutions in an inert solvent, but preferably without solvent.

Suitable radicals D or DB are for example:

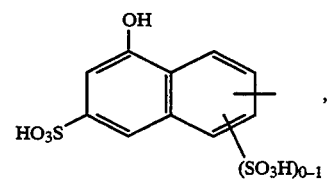

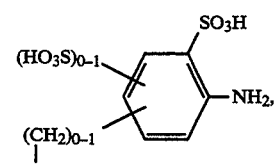

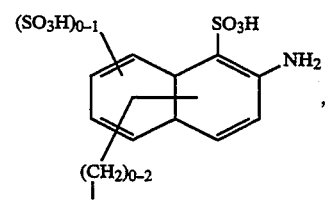

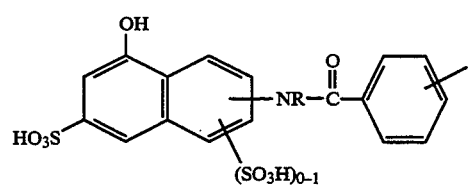

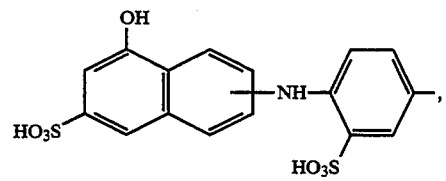

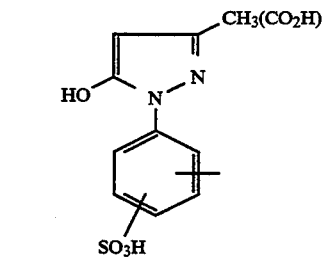

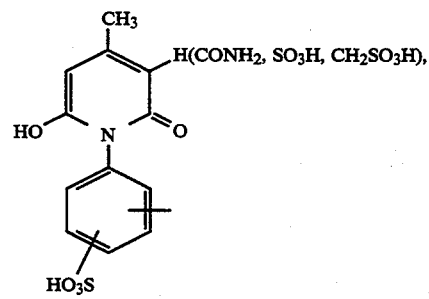

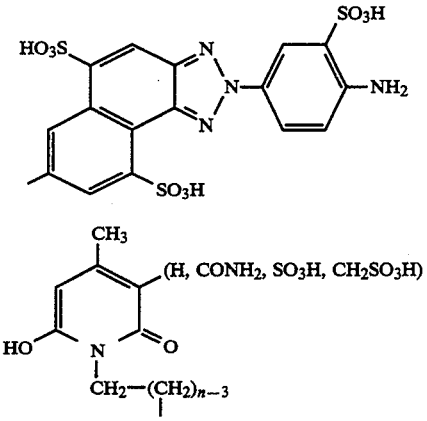

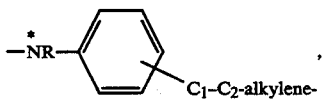

Suitable bridge members B are for example —COCH$_2$—, —C$_1$–C$_3$-alkylene—, —SO$_2$CH$_2$CH$_2$—, —CONRCH$_2$CH$_2$—, —SO$_2$NRCH$_2$CH$_2$—, —NR–C$_2$—C$_3$-alkylene,

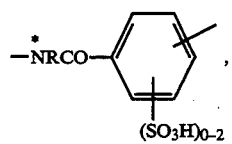

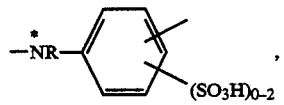

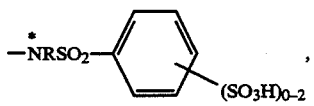

where the * indicates the point of attachment to D. Suitable sulpho group-containing aromatic amines (I) are for example 1,4-diaminobenzene-2,5-disulphonic acid, 1,3-diaminobenzene-4-sulphonic acid, 1,4-diaminobenzene-2-sulphonic acid, 1,3-diaminobenzene-4,6-disulphonic acid, 2,5-diaminobenzene-1,3-disulphonic acid, 1-amino-5-hydroxynaphthalene-7-sulphonic acid, 1-amino-8-hydroxynaphthalene-4-sulphonic acid, 1-amino-8-hydroxynaphthalene-3-sulphonic acid, 1-amino-8-hydroxynaphthalene-5-sulphonic acid, 2-amino-5-hydroxynaphathalene-7-sulphonic acid, 2-amino-6- hydroxynaphthalene-8-sulphonic acid, 2-amino-8-hydroxynaphthalene-6-sulphonic acid, 2-methylamino-5-hydroxynaphthalene-7-sulphonic acid, 2-ethylamino-5-hydroxynaphthalene-7-sulphonic acid, 2-methylamino-8-hydroxynaphthalene-6-sulphonic acid, 2-ethylamino-8-hydroxynaphthalene-6-sulphonic acid, 1-amino-6-hydroxynaphthalene-3,8-disulphonic acid, 1-amino-8-hydroxynaphthalene-3,6-disulphonic acid, 1-amino-8-hydroxy-naphthalene-2,4-disulphonic acid, 1-amino-8-hynaphthalene-4,6-disulphonic acid, 1-amino-8-hydroxynaphthalene-3,5-disulphonic acid, 2-amino-5-hydroxynaphthalene-1,7-disulphonic acid, 2-amino-8-hydroxynaphthalene-3,6-disulphonic acid, 2-amino-5-aminomethylnaphthalene-1-sulphonic acid, 8-( 4-aminobenzoyl )amino-1-hydroxynaphthalene-3,5-disulphonic acid, 8-(2-aminobenzoyl)amino-1-hydroxynaphthalene-3,5-disulphonic acid, 8-(4-aminobenzoyl)amino-1-hydroxy-naphthalene-3,6-disulphonic acid, 8-(2-aminobenzoyl)amino-1-hydroxynaphthalene-3,6-disulphonic acid, 8-(3-aminobenzoyl)amino-1-hydroxynaphthalene-3,6-disulphonic acid 7-(4-aminobenzoyl)amino-1-hydroxynaphthalene-3-sulphinic acid, 6-(2-aminobenzoyl )amino-1-hydroxynaphthalene-3-sulphonic acid, 6-(4-amino-2-sulphophenyl )amino-1-hydroxynaphthalene-3-sulphonic acid, 7-(4-amino-2-sulphophenyl)amino-1-hydroxynaphthalene-3-sulphonic acid.

Suitable chromophore compounds of the type (I)

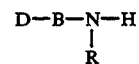  (I)

are for example

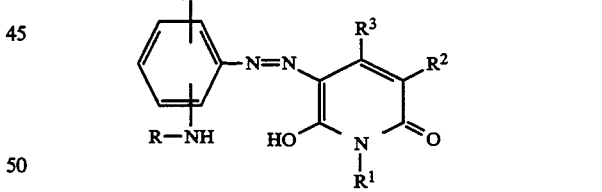 (IX)

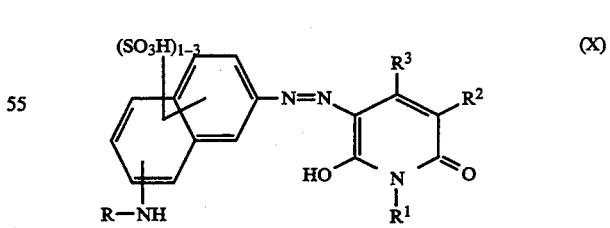 (X)

in which

R has the meaning give above,

R$^1$=H, C$_1$–C$_4$-alkyl, aryl, β-sulphoethyl,

R$^2$=H, C$_1$, SO$_3$H, CONH$_2$, CH$_2$SO$_3$H, CH$_3$ and SO$_2$CH$_3$,

R$^3$=H, CH$_3$, CH$_2$—$so_3$H, CO$_2$H,

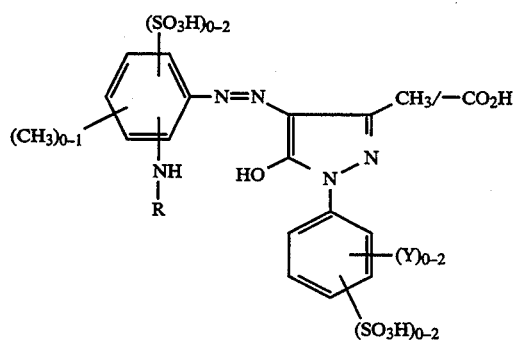
(XI)

in which
Y=chlorine or methyl,

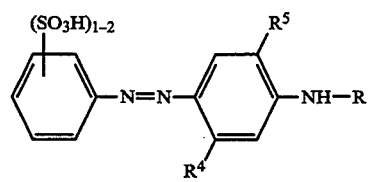
(XII)

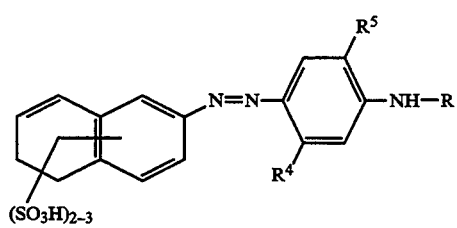
(XIII)

in which
R⁴=H, methyl, ethyl, methoxy, ethoxy, acetylamino, ureido, unsubstituted or substituted phenylcarbonylamino, mesylamino, halogen,
R⁵=H, methyl, ethyl, methoxy, ethoxy, sulpho,

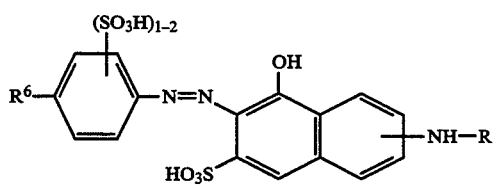
(XIV)

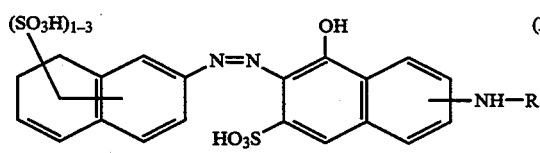
(XV)

in which
R⁶=H, methyl, ethyl, methoxy, ethoxy, chlorine or acetylamino,

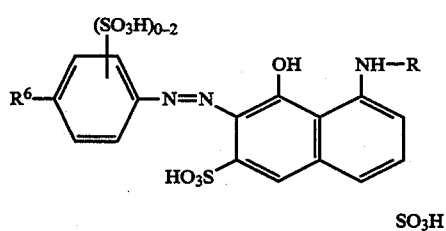
(XVI)

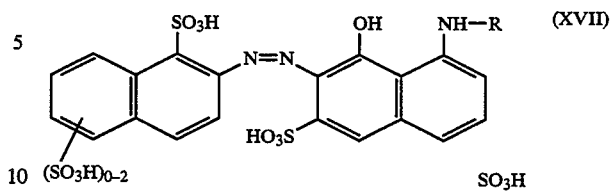
(XVII)

in which
R⁶ has the meaning given above,

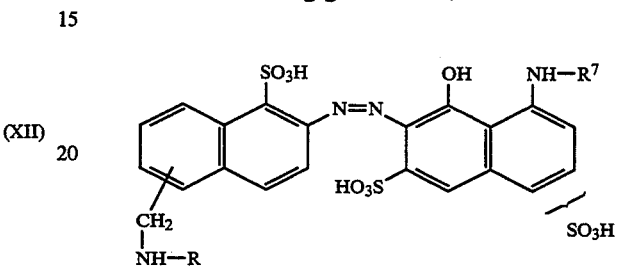

in which
R⁷=

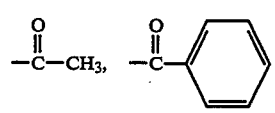

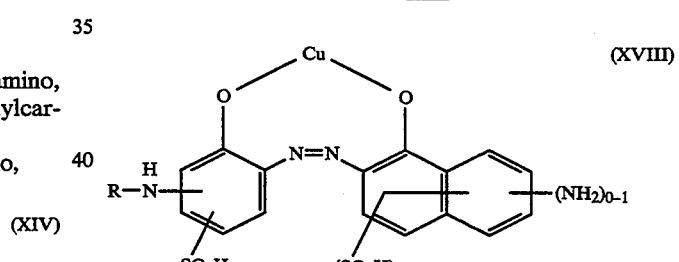
(XVIII)

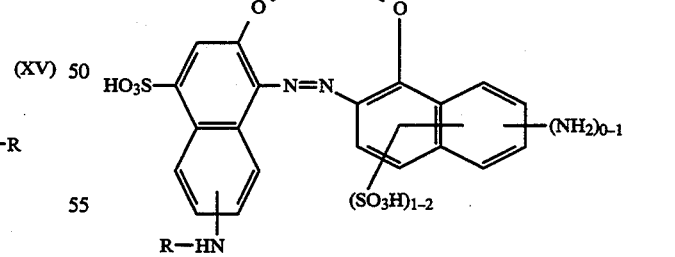
(XIX)

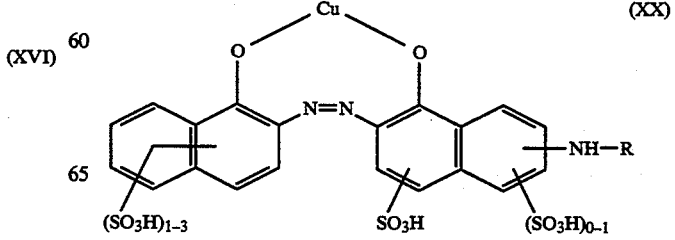
(XX)

-continued

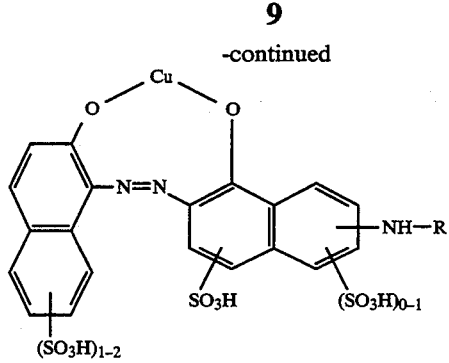
(XXI)

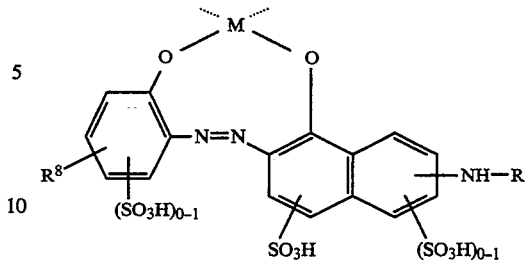
(XXIII)

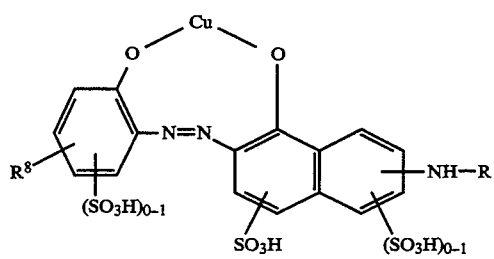
(XXII)

in which
R⁸ H, halogen, nitro or $C_1$-$C_4$-alkyl and
a) 1:2 Cr complexes or Co complexes of (XXIII), which contain two identical dyes (XXIII) or two different dyes (XXIII), or
b) 1:2 Cr complexes or Co complexes of (XXIII) with any other metal complex-forming dye,

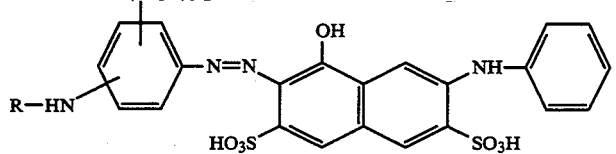
(XXIV)

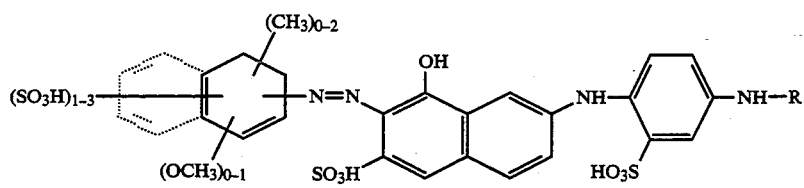
(XXV)

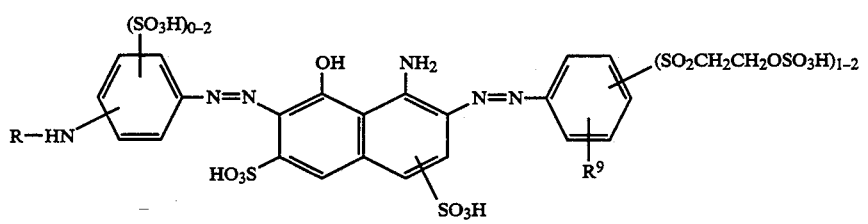
(XXVI)

in which
$R^9$=H, Cl, Br, methyl, methoxy, carboxy, sulpho,

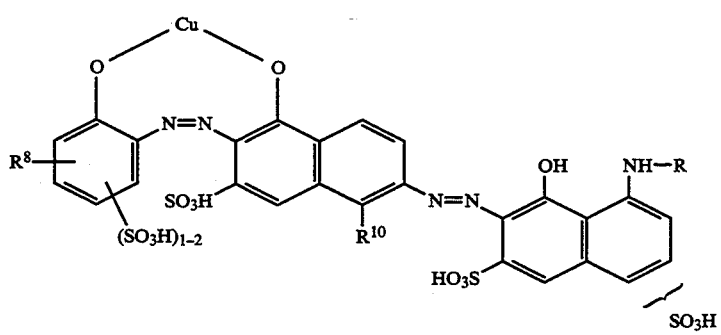
(XXVII)

in which
$R^{10}$= H or $SO_3H$ and R meaning given above,

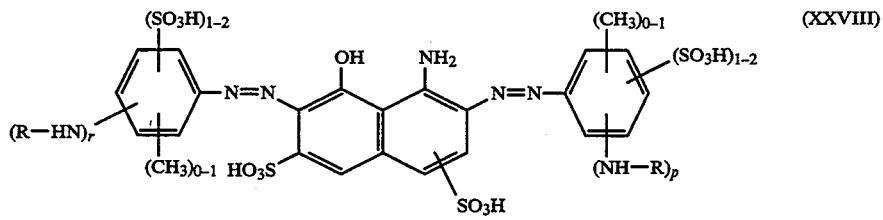  (XXVIII)
in which
r and p=0 or 1, where the sum
r+p=1 or 2,
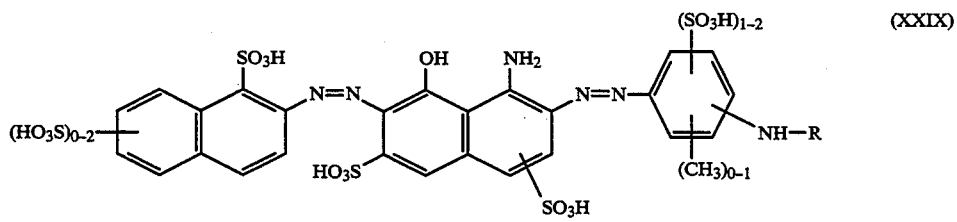  (XXIX)
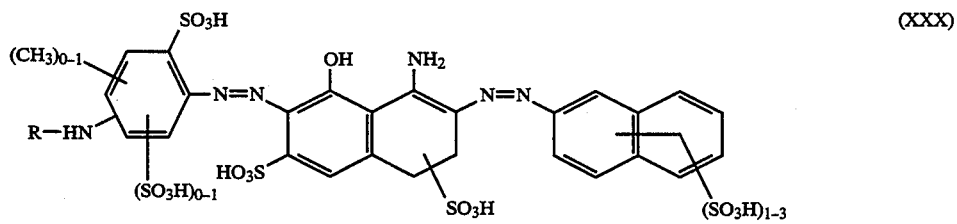  (XXX)
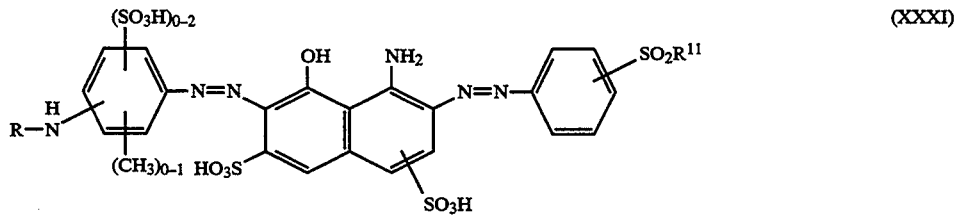  (XXXI)
in which
$R^{11}$ = —NH$_2$, —NHCH$_3$, —CH$_3$, —C$_2$H$_5$, —CH$_2$CH$_2$OH, —CHCH$_2$OH, —CH$_2$—CHOH, —OH,
$\phantom{R^{11} = —NH_2, —NHCH_3, —CH_3, —C_2H_5, —CH_2CH_2OH, —CHCH_2OH,\ }$ CH$_3$ $\phantom{—CH_2—}$ CH$_3$
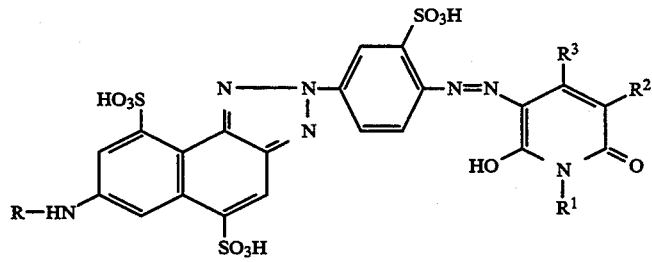
in which $R^1$, $R^2$, $R^3$ have the meaning given under formulae (IX) and (X),
(XXXII)
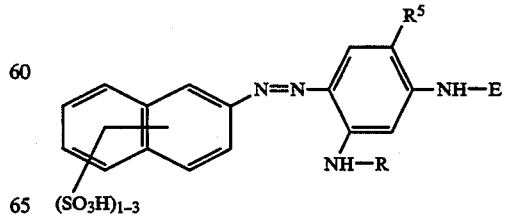
in which E=H, COCH$_3$ or COC$_6$H$_5$ and $R^5$ has the meaning given under formula (XII),

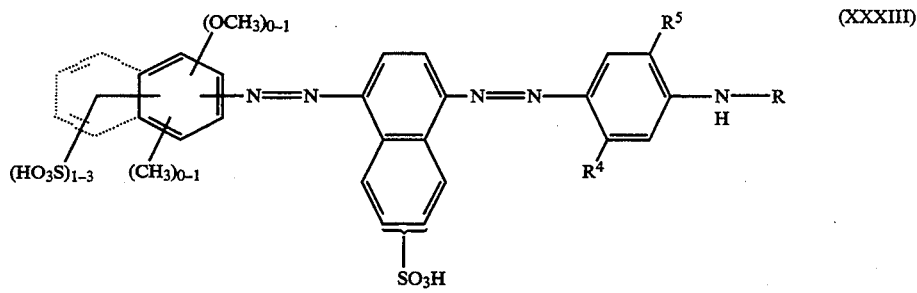
(XXXIII)
and $R^4$ and $R^5$ have the meaning given under formula (XII),
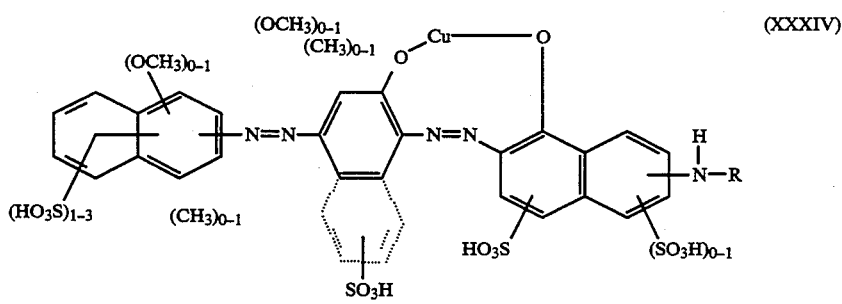
(XXXIV)
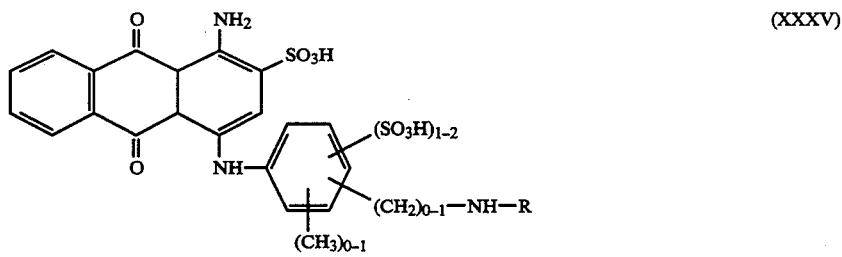
(XXXV)
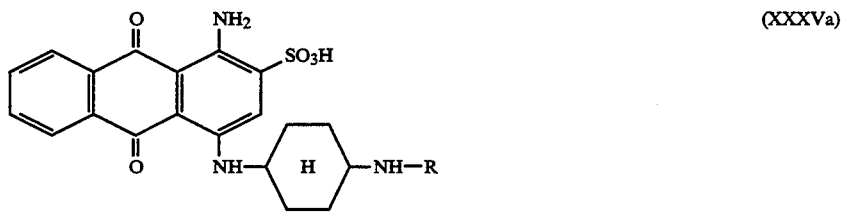
(XXXVa)
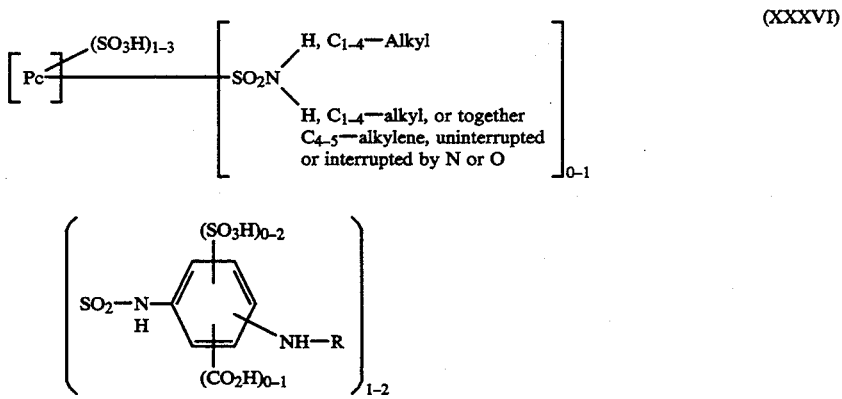
(XXXVI)
in which Pc represents a Cu- or Ni-phthalocyanine radical. The total number of substituents on the Pc skeleton is 4 in this case.

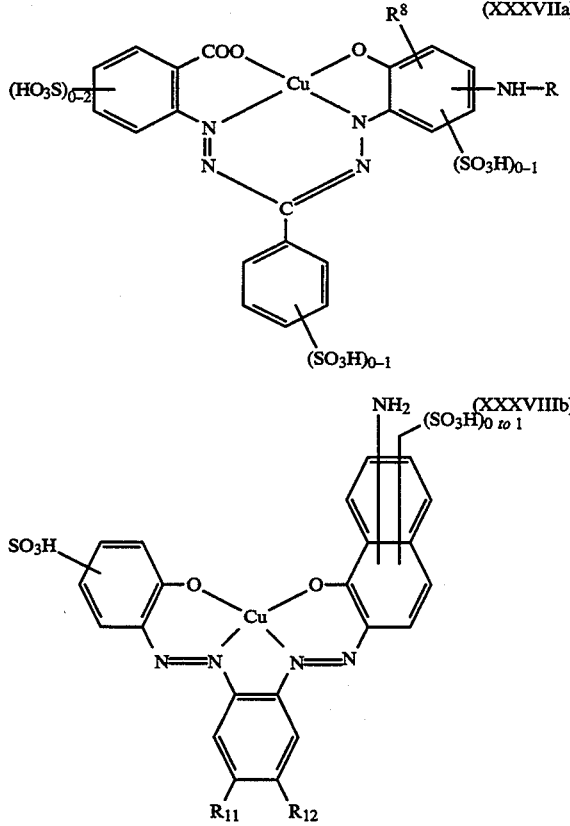
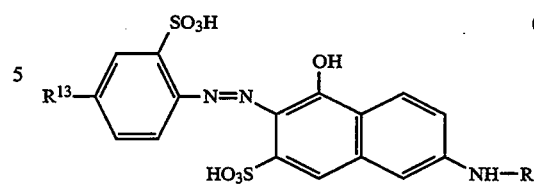
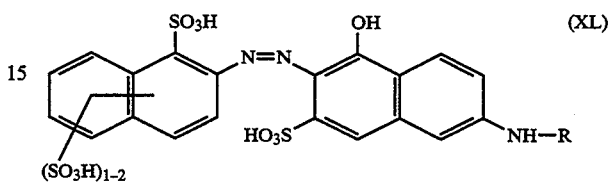
in which $R^{13}$ = H, $CH_3$, $H_3$, $OC_2H_5$ and $NHCOCH_3$
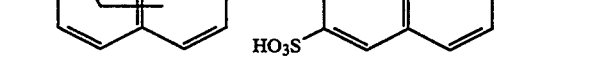
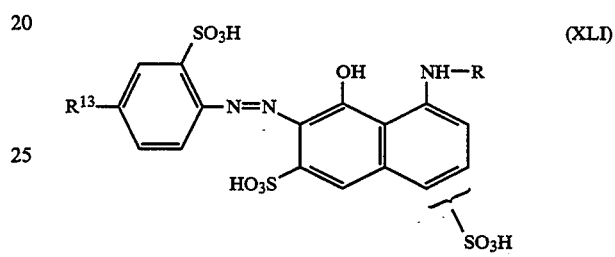
in which $R^{13}$ has the meaning given under formula (XXXIX),
in which
  $R_{11}$ = $C_1$-$C_4$-alkyl, halogen, —$OC_1$-$C_4$-alkyl, and
  $R_{12}$ = $OC_1$-$C_4$-alkyl
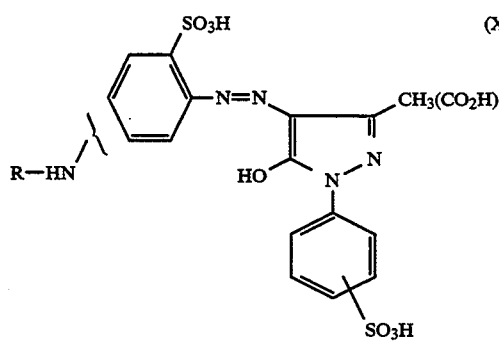
in which $R^8$ has the meaning given under formula (XXII),
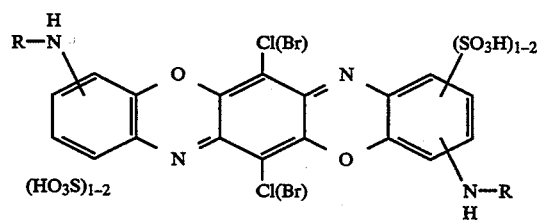
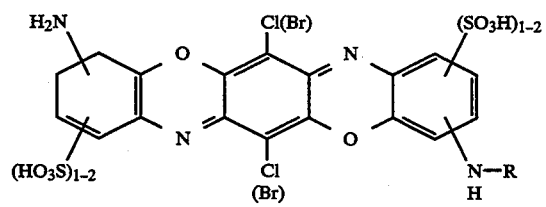

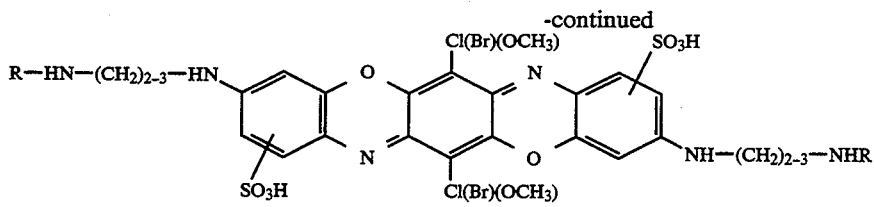

Suitable halogenopyrimidine radicals Z are:
2,4-Dichloro-6-pyrimidinyl-, 2,4,5-trichloro-6-pyrimidinyl-, 2,4-dichloro-5-nitro- or -5-methyl or -5-carboxymethyl- or -5-carboxy- or -5-cyano- or -5-vinyl- or -5-sulpho- or -5-mono-, -di- or -tri-chloromethyl- or -5-carbalkoxy-6-pyrimidinyl- and also the corresponding bromine and fluorine derivatives of the abovementioned pyrimidinyl radicals, among these for example 2-fluoro-4-pyrimidinyl-, 5,6-difluoro-4-pyrimidinyl-, 6-fluoro-5-chloro-4-pyrimidinyl-, 2,6-difluoro-4-pyrimidinyl-, 2,6-difluoro-5-chloro-4-pyrimidinyl-, 2-fluoro-5,6-dichloro-4-pyrimidinyl-, 2,6-difluoro-5-methyl-4-pyrimidinyl-, 2-fluoro-5-chloro-6-methyl-4-pyrimidinyl-, 2-fluoro-5-methyl-6-chloro-4-pyrimidinyl-, 2-fluoro-5-nitro-6-chloro-4-pyrimidinyl-, 5-bromo-2-fluoro-4-pyrimidinyl-, 2-fluoro-5-cyano-4-pyrimidinyl-, 2-fluoro-5-methyl-4-pyrimidinyl-, 2,5,6-trifluoro-4-pyrimidinyl-, 5-chloro-6-chloromethyl-2-fluoro-4-pyrimidinyl-, 5-chloro-6-dichloromethyl-2-fluoro-4-pyrimidinyl-, 5-chloro-6-trichloromethyl-2-fluoro-4-pyrimidinyl-, 5-chloro-2-chloromethyl-6-fluoro-4-pyrimidinyl-, 5-chloro-2-dichloromethyl-6-fluoro-4-pyrimidinyl-, 5-chloro-2-trichloromethyl-6-fluoro-4-pyrimidinyl-, 5-chloro-2-fluoro-dichloromethyl-6-fluoro-4-pyrimidinyl-, 2,6-difluoro-5-bromo-4-pyrimidinyl-, 2-fluoro-5-bromo-6-methyl-4-pyrimidinyl-, 2-fluoro-5-bromo-6-chloromethyl-4-pyrimidinyl-, 2,6-difluoro-5-chloromethyl-4-pyrimidinyl-, 2,6-difluoro-5-nitro-4-pyrimidinyl-, 2-fluoro-6-methyl-4-pyrimidinyl-, 2-fluoro-5-chloro-6-methyl-4-pyrimidinyl-, 2-fluoro-5-chloro-4-pyrimidinyl-, 2-fluoro-6-chloro-4-pyrimidinyl-, 6-trifluoromethyl-5-chloro-2-fluoro-4-pyrimidinyl-, 6-trifluoromethyl-2-fluoro-4-pyrimidinyl-, 2-fluoro-5-nitro-4-pyrimidinyl-, 2-fluoro-5-trifluoromethyl-4-pyrimidinyl-, 2-fluoro-5-phenyl- or -5-methylsulphonyl-4-pyrimidinyl-, 2-fluoro-5-carboxamido-4-pyrimidinyl-, 2-fluoro-5-carbomethoxy-4-pyrimidinyl, 2-fluoro-5-bromo-6-trifluoromethyl-4-pyrimidinyl-, 2-fluoro-6-carboamido-4-pyrimidinyl-, 2-fluoro-6-carbomethoxy-4-pyrimidinyl-, 2-fluoro-6-phenyl-4-pyrimidinyl-, 2-fluoro-6-cyano-4-pyrimidinyl-, 5-chloro-6-fluoro-2-methyl-4-pyrimidinyl-, 5,6-difluoro-2-trifluoromethyl-4-pyrimidinyl-, 5-chloro-6-fluoro-2-dichlorofluoromethyl-4-pyrimidinyl-, 2-fluoro-5-chloropyrimidin-4-yl, 2-methyl-4-fluoro-5-methylsulphonyl-6-pyrimidinyl-, 2,6-difluoro-5-methylsulphonyl-4-pyrimidinyl-, 2,6-dichloro-5-methylsulphonyl-4-pyrimidinyl-, 2-fluoro-5-sulphonamido-4-pyrimidinyl-, 2-fluoro-5-chloro-6-carbomethoxy-4-pyrimidinyl-, 2,6-difluoro-5-trifluoromethyl-4-pyrimidinyl; sulpho group-containing triazine radicals, such as 2,4-bis-(phenylsulphonyl)-triazinyl-6-, 2-(3'-carboxyphenyl)-sulphonyl-4-chlorotriazinyl-6-, 2-(3'-sulphophenyl)-sulphonyl-4-chlorotriazinyl-6-, 2,4-bis-(3'-carboxyphenylsulphonyl)-triazinyl-6; sulphonyl group-containing pyrimidine rings, such as 2-carboxymethylsulphonyl-4-pyrimidinyl-, 2-methylsulphonyl-6-methyl-4-pyrimidinyl-, 2-methylsulphonyl-6-ethyl-4-pyrimidinyl-, 2-phenylsulphonyl-5-chloro-6-methyl-4-pyrimidinyl-, 2,6-bis-methylsulphonyl-4-pyrimidinyl-, 2,6-bis-methylsulphonyl-5-chloro-4-pyrimidinyl-, 2,4-bis-methylsulphonyl-pyrimidin-5-sulphonyl-, 2-methylsulphonyl-4-pyrimidinyl-, 2-phenyl-sulphonyl-4-pyrimidinyl-, 2-trichloromethylsulphonyl-6-methyl-4-pyrimidinyl-, 2-methylsulphonyl- 5-chloro-6-methyl-4-pyrimidinyl-, 2-methylsulphonyl-5-bromo-6-methyl-4-pyrimidinyl-, 2-methylsulphonyl-5-chloro-6-ethyl-4-pyrimidinyl-, 2-methylsulphonyl-5-chloro-6-chloromethyl-4-pyrimidinyl-, 2-methylsulphonyl-4-chloro-6-methylpyrimidin-5-sulphonyl-, 2-methylsulphonyl-5-nitro-6-methyl-4-pyrimidinyl-, 2,5,6-tris-methylsulphonyl-4-pyrimidinyl-, 2-methylsulphonyl-5,6-dimethyl-4-pyrimidinyl-, 2-ethylsulphenyl-5-chloro-6-methyl-4-pyrimidinyl-, 2-methylsulphonyl-6-chloro-4-pyrimidinyl-, 2,6-bis-methylsulphonyl-5-chloro-4-pyrimidinyl-, 2-methylsulphonyl-6-carboxy-4-pyrimidinyl-, 2-methylsulphonyl-5-sulpho-4-pyrimidinyl-, 2-methylsulphonyl-6-carbomethoxy-4-pyrimidinyl-, 2-methylsulphonyl-5-carboxy-4-pyrimidinyl-, 2-methylsulphonyl-5-cyano-6-methoxy-4-pyrimidinyl-, 2-methylsulphonyl-5-chloro-4-pyrimidinyl-, 2-β-sulphoethylsulphonyl-6-methyl-4-pyrimidinyl-, 2-methylsulphonyl-5-bromo-4-pyrimidinyl-, 2-phenylsulphonyl-5-chloro-4-pyrimidinyl-, 2-carboxymethylsulphonyl-5-chloro-6-methyl-4-pyrimidinyl-, 2-methylsulphonyl-6-chloro-4-pyrimidinyl.

Particularly suitable are the halogenopyrimidines (Hal-Z) of the formulae:

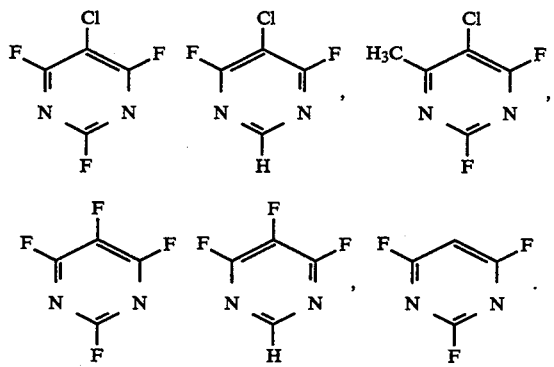

EXAMPLE 1

In a jet nozzle reactor according to FIG. 1, 9 kg/hour of 5-chloro-2,4,6-trifluoropyrimidine at 20° C. and also 171 l/hour of a warm, 40° C., aqueous solution of 12.9 kg of 7-amino-4-hydroxynaphthalene-2-sulphonic acid Na salt and 2.1 kg of sodium fluoride are fed simultaneously and continuously via separate feed lines in such a manner that the 5-chloro-2,4,6-trifluoropyrimidine enters the flowing aqueous solution with a pressure drop of 35 bar. After exit from the jet nozzle reactor, the reaction is completed in a residence time length or in a stirred vessel cascade. The solution thus obtained, after cooling to 0° C., is reacted in the conventional manner with the diazonium salt of 2-amino-5-methoxy-benzenesulphonic acid and, after salting out with sodium chloride, the reactive dye of the formula

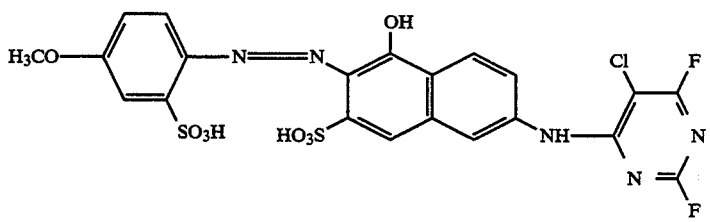

which dyes cotton in clear scarlet shades, is obtained in good yields.

EXAMPLE 2

9 kg/hour of 5-chloro-2,4,6-trifluoropyrimidine at 20° C. and also 120 l/hour of a warm, 30° C. aqueous solution of 12.48 kg of 2-amino-5-aminomethyl-naphthalene-1-sulphonic acid and 4.4 kg of sodium hydroxide are fed simultaneously and continuously into a rotor/stator mixer type of dispersion unit. After exit from the rotor/stator mixer, the reaction is completed in a residence time length or in a stirred container After cooling to 0° C. the suspension thus obtained is adjusted to a pH of about 1.5 with hydrochloric acid and sodium nitrite is added. The diazonium salt thus obtained is coupled in a conventional manner to 8-benzoylamino-1-hydroxy-naphthalene-3,5-disulphonic acid. Following isolation, good yields are obtained of the reactive dye of the formula

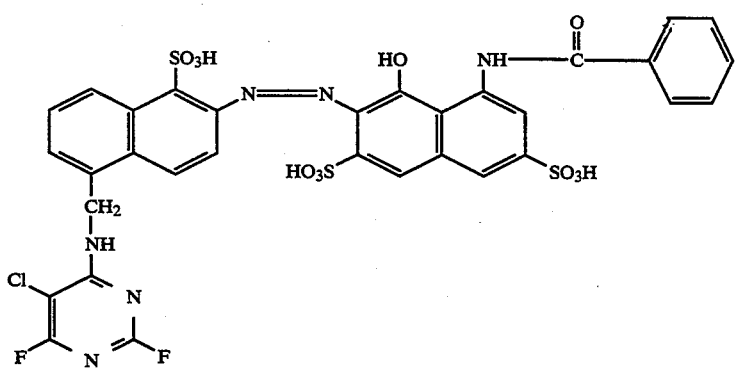

which dyes cotton in red shades with good fastness.

EXAMPLE 3

9.5 kg/hour of 4,6-difluoro-5-chloropyrimidine having a temperature of 20° C., and 188 l/hour of an aqueous solution at 50° C., containing 11.3 kg of 1,3-diamino-benzene-6-sulphonic acid and 2.4 kg of sodium hydroxide are introduced simultaneously and continuously into a jet nozzle reactor according to FIG. 1 in such a manner that the 4,6-difluoro-5-chloropyrimidine enters into the flowing solution with a pressure drop of 30 bar. After exit from the reactor, the reaction is completed in a residence time length or in a vessel cascade. The product of the reaction is then salted out in a conventional manner with sodium chloride and isolated or further processed without isolation.

The intermediate with the formula below

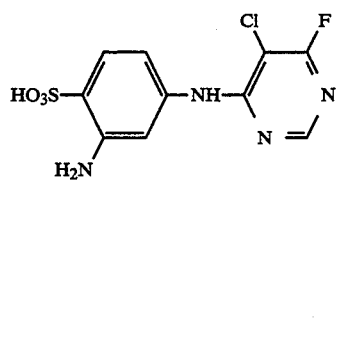

is used in conventional processes to form reactive dyes.

EXAMPLE 4

9.0 kg/hour of 2,4,6-trifluoropyrimidine having a temperature of 20° C., and 430 l/hour of an aqueous solution at 50° C., containing 41.7 kg of dye base of the formula

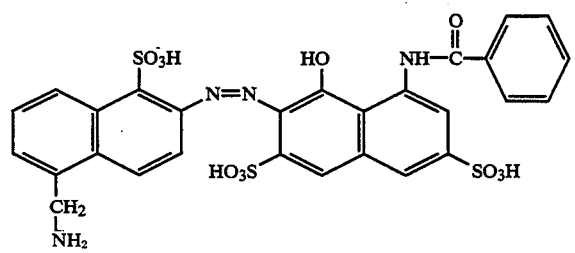

and 9.6 kg of sodium hydroxide are introduced simultaneously and continuously into a jet nozzle reactor according to FIG. 1 via separate feeders in such a manner that the 2,4,6-trifluoropyrimidine enters into the flowing solution with a pressure drop of 30 bar. After exit from the reactor, the reaction is completed in a residence time length or in a vessel cascade. The product of the reaction is then in a conventional manner salted out using sodium chloride and isolated.

The dye of the formula

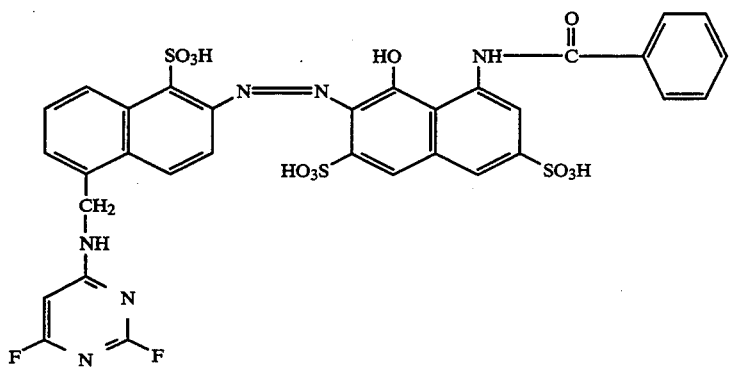

dyes cellulose in red shades with very high wetfastness.

EXAMPLE 5

9.5 kg/hour of 5-chloro-2,4,6-trifluoropyrimidine having a temperature of 20° C. and 455 l/hour of an aqueous solution at 45° C. containing 35.9 kg of the disodium salt of the dye base of the formula

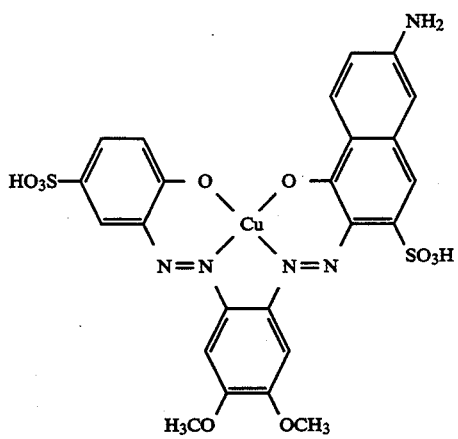

and 7.2 kg of disodium hydrogen phosphate are introduced simultaneously and continously into a jet nozzle reactor according to FIG. 1 via separate feeders in such a manner that the 5-chloro-2,4,6-trifluoropyrimidine enters into the flowing solution with a pressure drop of 30 bar. After exit from the reactor, the reaction is completed in a residence time length or in a vessel cascade. The product of the reaction is then in a conventional manner salted out using sodium chloride and isolated.

The dye of the formula

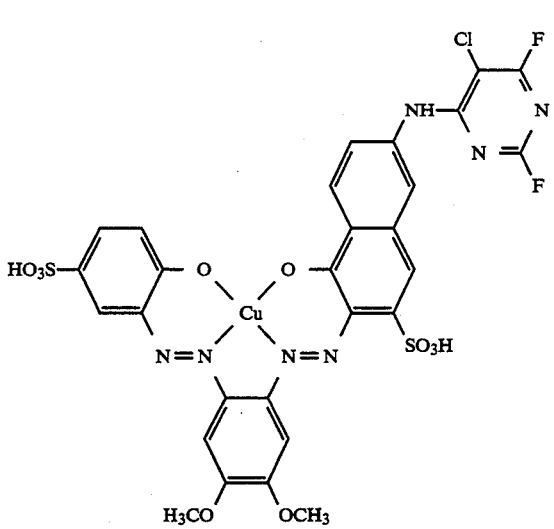

dyes cellulose in olive shades with very high wetfastness.

EXAMPLE 6

9.5 kg/hour of 5-chloro-2,4,6-trifluoropyrimidine having a temperature of 20° C., and 118 l/hour of an aqueous solution at 40° C., containing 29.3 kg of the disodium salt of the dye base of the formula and 2.2 kg of sodium hydroxide are introduced simultaneously and continuously into a jet nozzle reactor according to FIG. 1 in such a manner that the 5-chloro-2,4,6-trifluoropyrimidine enters into the flowing solution with a pressure drop of 30 bar. After exit from the reactor, the reaction is completed in a residence time length or in a vessel cascade. The product of the reaction is then in a conventional manner salted out using sodium chloride and isolated.

The dye of the formula

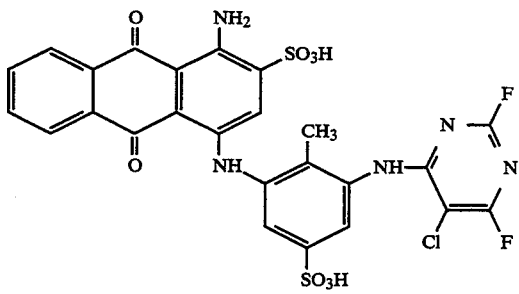

dyes cellulose in blue shades with very high wetfastness.

EXAMPLE 7

9.5 kg/hour of 5-chloro-2,4,6-trifluoropyrimidine having a temperature of 20° C., and 50 l/hour of an aqueous solution at 30° C., containing 5.79 kg of 1,3-diaminobenzene and at a pH of 7.0 are simultaneously and continuously introduced into a jet nozzle reactor according to FIG. 1 in such a manner that the 5-chloro-2,4,6,-trifluoropyrimidine enters into the flowing solution with a pressure drop of 30 bar. After exit from the reactor, the reaction is completed in a residence time length or in a vessel cascade. The reaction product is then reacted in a conventional manner with the dye base of the structure below

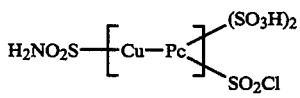

to give the reactive dye of the formula

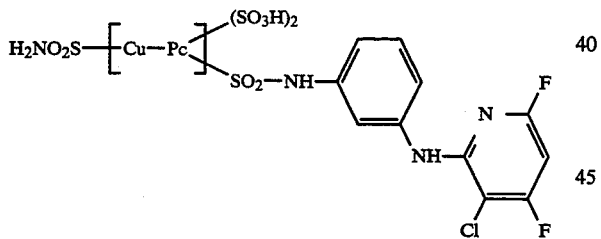

which dyes cellulose in turquoise-blue shades with very high wetfastness.

We claim:

1. Process for the continuous reaction of halogenopyrimidine with amines, halogenopyrimidine and an aqueous amine solution or suspension being passed into a reactor via separate feed lines and the reaction product being subsequently conducted away, characterised in that the starting materials are introduced into the reactor simultaneously and continuously with intensive mixing and with flow substantially free from backmixing.

2. Process according to claim 1, characterised in that the reactor used is a dispersion unit of the rotor/stator mixer type, the halogenopyrimidine flowing into the reactor with a Reynolds number of at least 2,500 and the aqueous amine solution flowing into the reactor with a Reynolds number of at least 2,500.

3. Process according to claim 1, characterised in that the reactor used is a reaction tube into which open one or more nozzles, the amine solution flowing into the reactor via the reaction tube with a Reynolds number of at least 2,500, the halogenopyrimidine flowing into the reactor via the nozzle or nozzles with a Reynolds number of at least 10,000, the difference in flow velocities between the halogenopyrimidine stream and amine solution stream being at least 20 m/s.

4. Process according to claim 3, characterised in that a ratio of reactor cross-sectional area $F_R$ to inlet cross-sectional area $F_1$ of the halogenopyrimidine stream of 225 to 40,000 is maintained.

5. Process according to claim 1, characterised in that a halogenopyrimidine Hal-Z is reacted with an amine of the formula

to give reactive substances or reactive dye precursors of the formula

in which
B represents a direct linkage or bridge member to an aromatic carbocyclic C atom of the radical D,
R represents H, unsubstituted or substituted $C_1$-$C_4$-alkyl, unsubstituted or substituted phenyl,
D represents a radical of the benzene, naphthalene or heterocyclic series
Z represents mono-, di- and trihalogenopyrimidinyl radicals,
Hal represents —F, —Cl and —Br.

6. Process according to claim 1,
characterised in that the amine has at least one of the radicals below

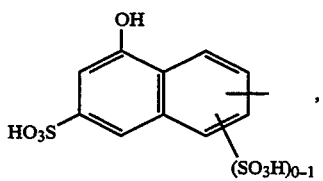

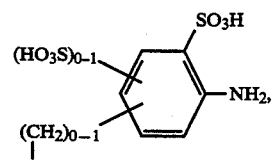

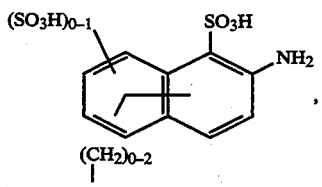

-continued
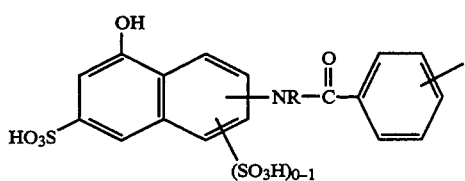
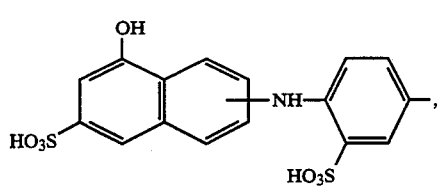
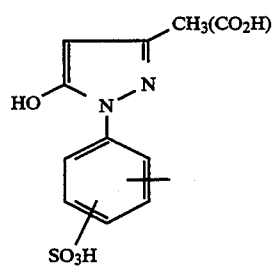
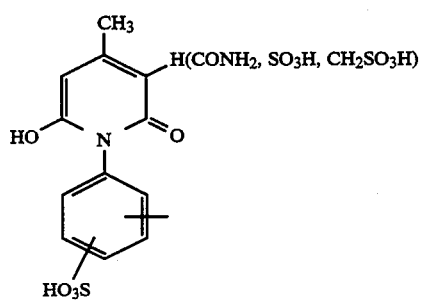
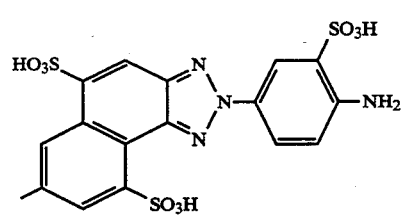
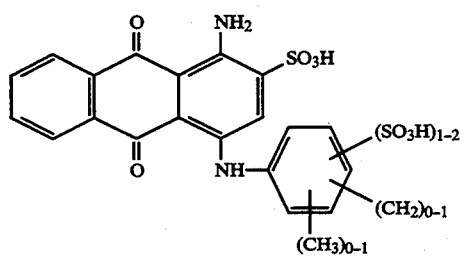
-continued
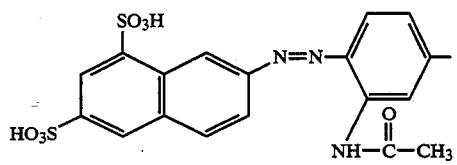
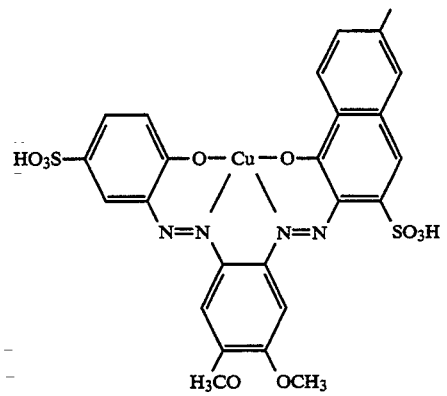
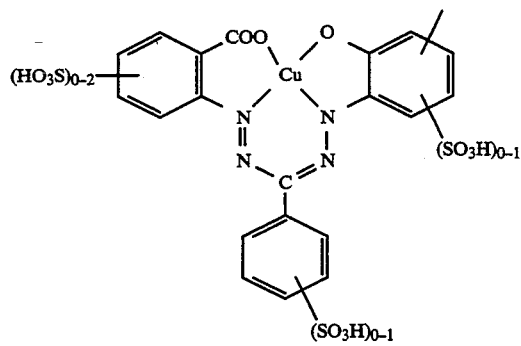
7. Process according to claim 1, characterised in that the halogenopyrimidine corresoonds to at least one of the formulae below
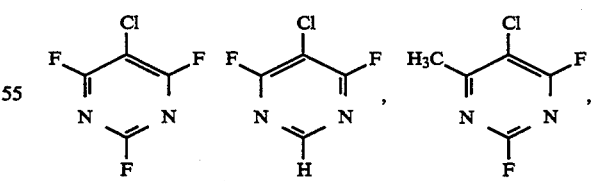
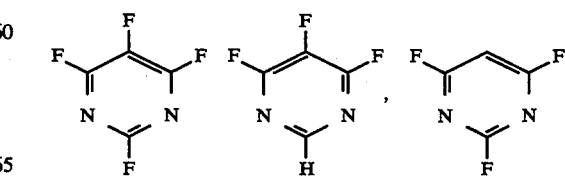
* * * * *

UNITED STATES PATENT AND TRADEMARK OFFICE
CERTIFICATE OF CORRECTION

PATENT NO. : 5,420,255
DATED : May 30, 1995
INVENTOR(S) : Arnold, et al.

It is certified that error appears in the above-indentified patent and that said Letters Patent is hereby corrected as shown below:

Title Page, Item [75] Inventors: After fourth Inventor " Mullers " insert -- Bergisch --

Col. 25, line 64  Delete " $(CH_2)_{0-1}$" and substitute -- $(CH_2)_{\overline{0}-1}$ --

Col. 26, line 49  Delete " corresoonds " and substitute -- corresponds --

Signed and Sealed this

Twenty-sixth Day of September, 1995

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO : 5,420,255
DATED : May 30, 1995
INVENTOR(S): Arnold, et al.

It is certified that error appears in the above-identified patent and that said Letters Patent is hereby corrected as shown below:

| | |
|---|---|
| Col. 3, line 41 | After " carbocyclic " delete " ; " |
| Col. 5, line 21 | Delete " $-COCH_2-$, " and substitute -- $-\overset{*}{C}OCH_2-$, -- ; delete " $-SO_2CH_2CH_2-$, " and substitute -- $\overset{*}{S}O_2CH_2CH_2-$, -- |
| Col. 5, line 22 | Delete " $-CONRCH_2CH_2-$, " and substitute -- $-\overset{*}{C}ONRCH_2CH_2-$, --: delete " $-SO_2NRCH_2CH_2-$, " and substitute -- $\overset{*}{S}O_2NRCH_2CH_2-$, -- |
| Col. 5, lines 22-23 | Delete " $-NR-C_2-C_3-alkylene$, " and substitute -- $-\overset{*}{N}R-C_2-C_3-alkylene$, -- |
| Col. 6, line 25 | After " acid " insert -- , -- |
| Col. 6, line 65 | Delete " $C_1$ " and substitute -- Cl -- |
| Col. 6, last line | Delete " $CH_2-so_3H$, " and substitute -- $CH_2-SO_3H$, -- |

UNITED STATES PATENT AND TRADEMARK OFFICE
CERTIFICATE OF CORRECTION

PATENT NO : 5,420,255
DATED : May 30, 1995
INVENTOR(S): Arnold, et al.

Page 2 of 5

It is certified that error appears in the above-identified patent and that said Letters Patent is hereby corrected as shown below:

Col. 7, line 52 (XV)  Delete " 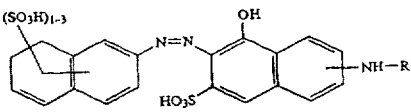 " and substitute -- 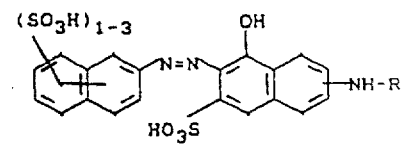 --

Col. 7, last line ((XVI)  Delete " 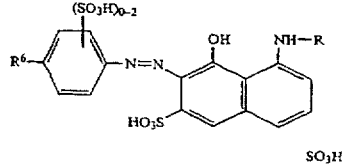 " and substitute -- 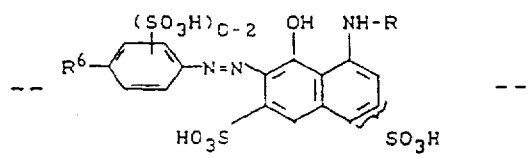 --

Col. 8, line 7 (XVII)  Delete " 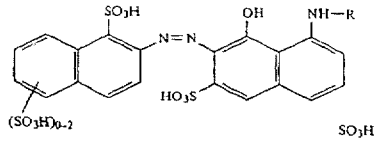 " and substitute -- 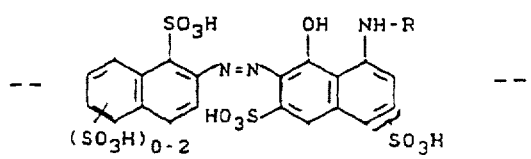 --

UNITED STATES PATENT AND TRADEMARK OFFICE
CERTIFICATE OF CORRECTION

PATENT NO : 5,420,255
DATED : May 30, 1995
INVENTOR(S): Arnold, et al.

It is certified that error appears in the above-identified patent and that said Letters Patent is hereby corrected as shown below:

Col. 9, line 6 (XXI)     Delete " 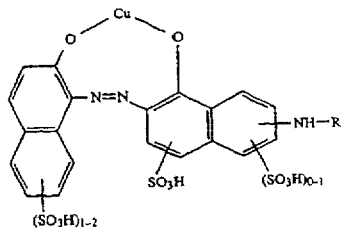 " and substitute

-- 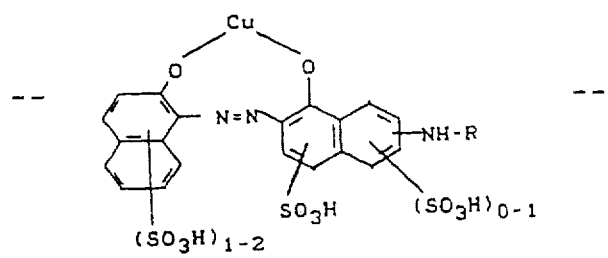 --

Col. 10, last line     Delete " Rmeaning " and substitute -- $R^8$ has the meaning --

Col. 11 Formula (XXX)     Delete " 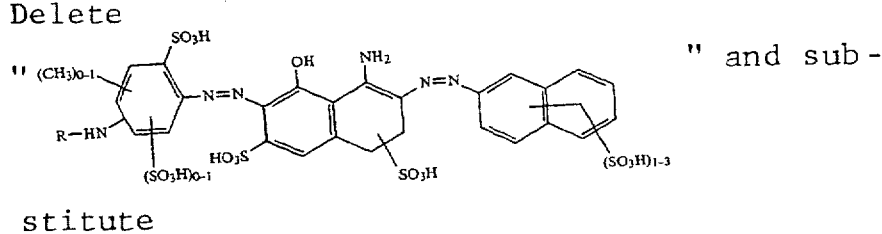 " and substitute

-- 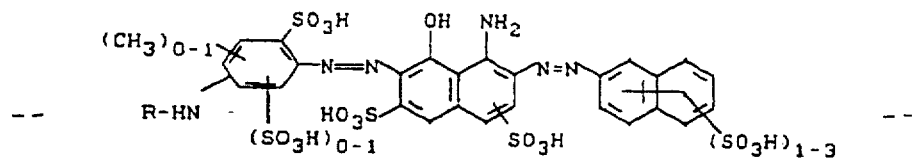 --

UNITED STATES PATENT AND TRADEMARK OFFICE
CERTIFICATE OF CORRECTION

PATENT NO : 5,420,255
DATED : May 30, 1995
INVENTOR(S): Arnold, et al.

It is certified that error appears in the above-identified patent and that said Letters Patent is hereby corrected as shown below:

Col. 12, line 62    After formula insert -- (XXXII) --

Col. 13, formula    Delete " 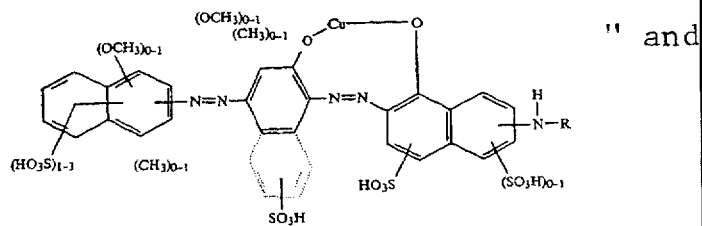 " and
(XXXIV)

substitute

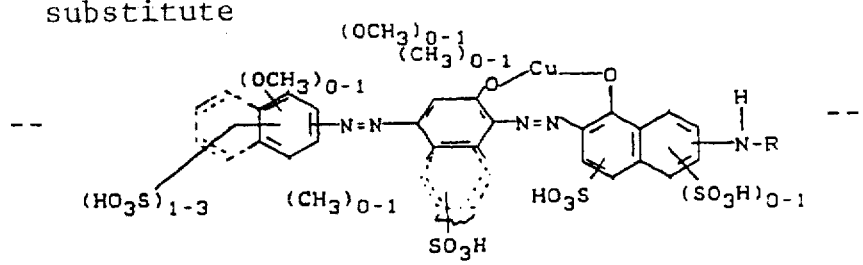

--

Col. 16, line 11    Delete " $H_3$ " and substitute -- $OCH_3$ --

Col. 16, formula    Delete " 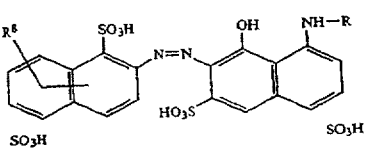 " and sub-
(XLII)

stitute -- 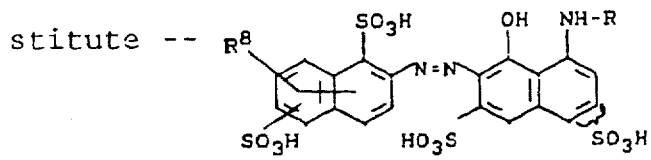 --

UNITED STATES PATENT AND TRADEMARK OFFICE
CERTIFICATE OF CORRECTION

PATENT NO : 5,420,255
DATED : May 30, 1995
INVENTOR(S): Arnold, et al.

It is certified that error appears in the above-identified patent and that said Letters Patent is hereby corrected as shown below:

Col. 15-16 formula Delete "  " and substitute -- --
(XLIII)

Signed and Sealed this

Twelfth Day of October, 1999

Attest:

Q. TODD DICKINSON

*Attesting Officer*      *Acting Commissioner of Patents and Trademarks*